US010844091B2

(12) United States Patent
Dejko et al.

(10) Patent No.: US 10,844,091 B2
(45) Date of Patent: Nov. 24, 2020

(54) PEPTIDE WITH ANTIDEPRESSANT ACTIVITY AND THERAPEUTIC EFFECT AGAINST ALZHEIMER'S DISEASE

(71) Applicant: "VERTA RESEARCH-PRODUCTION COMPANY" LTD, Sankt-Peterburg (RU)

(72) Inventors: Roman Danilovich Dejko, Har'kov (UA); Alexandr Alexandrovich Kolobov, Sankt-Peterburg (RU); Elena Arturovna Kampe-Nemm, Sankt-Peterburg (RU); Vladimir Michajlovich Shpen, Sankt-Peterburg (RU)

(73) Assignee: "VERTA RESEARCH-PRODUCTION COMPANY"LTD, Sankt-Peterburg (RU)

( * ) Notice: Subject to any disclaimer, the term of this patent is extended or adjusted under 35 U.S.C. 154(b) by 0 days.

(21) Appl. No.: 16/643,711

(22) PCT Filed: Jan. 29, 2018

(86) PCT No.: PCT/RU2018/000038
§ 371 (c)(1),
(2) Date: Mar. 2, 2020

(87) PCT Pub. No.: WO2018/199803
PCT Pub. Date: Nov. 1, 2018

(65) Prior Publication Data
US 2020/0231625 A1    Jul. 23, 2020

(30) Foreign Application Priority Data
Apr. 28, 2017 (RU) .................. 2017115294

(51) Int. Cl.
| A61K 38/06 | (2006.01) |
| A61K 38/07 | (2006.01) |
| C07K 5/08 | (2006.01) |
| C07K 5/10 | (2006.01) |
| C07K 5/00 | (2006.01) |
| C07K 5/11 | (2006.01) |
| C07K 5/103 | (2006.01) |

(52) U.S. Cl.
CPC .......... C07K 5/1019 (2013.01); C07K 5/1005 (2013.01)

(58) Field of Classification Search
CPC ... C07K 5/00; C07K 5/08; C07K 5/10; A61K 38/06; A61K 38/07
USPC ........ 514/17.8, 21.9, 1.1; 530/330, 331, 300
See application file for complete search history.

(56) References Cited

U.S. PATENT DOCUMENTS

| 4,966,848 | A | * | 10/1990 | Smith | .................. | C12N 9/1029 435/193 |
| 5,223,421 | A | * | 6/1993 | Smith | .................. | C12N 9/1029 435/193 |
| 5,837,218 | A | * | 11/1998 | Peers | .................. | A61K 51/088 424/1.69 |
| 2003/0050247 | A1 | * | 3/2003 | Kuhner | ..................... | A61P 9/00 514/2.4 |

FOREIGN PATENT DOCUMENTS

| RU | 2356573 C1 * | 5/2009 | ............. A61K 38/07 |
| RU | 2537560 C2 | 1/2015 | |
| RU | 2559880 C1 | 8/2015 | |
| WO | 2011/128455 A1 | 10/2011 | |

OTHER PUBLICATIONS

RU 2537560, machine translation, pp. 1-23, Jan. 10, 2015. (Year: 2015).*
Deiko R.D. et. al. Vliyanie potentsialnogo neiroprotektora acetyl-(d-lys)-lys-arg-arg-amide (kk-1) na neirodestruktsiju i neiroapoptoz u krys pri ostrom narushenii mozgovogo krovoobrascheniya/ Vestnik farmatsii #1 (71), 2016, p. 96-102.

* cited by examiner

*Primary Examiner* — Julie Ha
(74) *Attorney, Agent, or Firm* — Nadya Reingand; Yan Hankin (57) ABSTRACT

The invention includes a tetrapeptide to be used in the treatment of Alzheimer's disease and depression. The tetrapeptide comprises the general formula, acetyl-X-ARG-ARG-amide, where X=-(D-ARG)-ARG-; -(D-LYS)-LYS-; or -(D-MET)-MET-. On the basis of the combination of pharmacological properties identified, a preparation including the tetrapeptide has potential for clinical use as a nootropic, neuroprotective, and antidepressant agent.

1 Claim, 7 Drawing Sheets

Specification includes a Sequence Listing.

Fig.14

PEPTIDE WITH ANTIDEPRESSANT ACTIVITY AND THERAPEUTIC EFFECT AGAINST ALZHEIMER'S DISEASE

CROSS-REFERENCE TO RELATED APPLICATIONS

The present patent application is a National stage application for the PCT application PCT/RU2018/000038 filed Jan. 29, 2018 which claims priority to Russian patent application RU2017115294 filed Apr. 28, 2017, all of which are incorporated herein in their entirety.

FIELD OF THE INVENTION

The invention relates to biochemistry, specifically, to a novel biologically active compound, a peptide having a therapeutic effect on brain function disorders such as Alzheimer's disease that can be used to create a preparation for the treatment of such disorders.

BACKGROUND

Antidepressants are understood to be the psychotropic agents used in the treatment of depression by affecting the level of neurotransmitters, in particular serotonin, noradrenalin, and dopamine improving patients' mood, reducing anxiety, apathy, stress, etc. [https://en.wikipedia.org/wiki/Depressant]. Additionally, by maintaining the serotonin level, some antidepressants can improve the condition of patients suffering from Alzheimer's disease, especially after a stroke, by slowing plaque buildup in the brain [http://www.patronage.ru/news].

Alzheimer's disease (AD) is a severe neurodegenerative disorder resulting in memory loss, mental impairment, and inevitable death. Its main distinct pathological feature is an altered cytoskeleton in some susceptible neurons. These changes are not an inevitable result of aging; however, after the onset of the disease, no spontaneous recovery or remission is observed. The initial cortical changes described below develop in the poorly myelinated transentorhinal region of the medial temporal lobe. The destructive process then follows a predictable pattern as it spreads out into other cortical areas. The location of the tangle-forming neurons and the severity of changes can differentiate between six stages in the disease propagation: from stages I-II, which are not clinically presented, to stages V-VI with fully developed AD. A small number of cases present with particularly early changes indicating that advanced age is not a prerequisite for the evolution of the lesions. AD is thus an age-related, but not an age-dependent disease. Today, there are several theories as to the causes and mechanism of AD development; many of them attributing the disease to genetic defects.

Modern medical practice uses compensatory pharmaceutical preparations to treat AD symptoms. Such preparations can somewhat inhibit the disease progression but do not cure it.

Cholinesterase inhibitors (ChEI) are the most commonly used class of drugs [Watkins, P. B. et al. J. Am. Med. Assoc. 1994. V. 271. pp. 992-998]; they prolong the effect of the neurotransmitter acetylcholine on the postsynaptic receptors, which results in the increase of cholinergic innervation. However, the efficacy of ChEI significantly decreases at later AD stages. In addition, they are relatively toxic and cause several other adverse side effects.

A known symptomatic AD treatment is memantine, a glutamatergic system modulator [Raina P. at al//Ann. Intern. Med. 2008. V. 148 (5). pp 379-397]. The best results are achieved when said drug is used for the treatment of mild and moderate Alzheimer-type dementia. However, this medication does not completely cure AD. In particular, the disadvantages of the compensatory approach to treatment are that the methods developed within this approach do not inhibit AD propagation mechanism. Thus, there is an active research conducted today to find drugs for radical AD treatment that would not only compensate the symptomatic disorders but also cure the disease.

One contemporary hypothesis proposes that β-amyloid peptides, in particular βA-(1-42), can form clusters in the central nervous system in the form of amyloid plaques as a result of the impaired metabolism, which then leads to the destruction of brain tissue [Hardy J., Selkoe D. J. The amyloid hypothesis of Alzheimer's disease: progress and problems on the road to therapeutics. Science. 2002. V. 297 (5580). pp 353-356]. Based on this hypotheses, various immunotherapeutic techniques directed to the correction of the βA content in the human body for the prevention of AD development have been actively studied. Injection with βA-based preparations lead to the formation of specific antibodies that promote βA removal from the brain [Shenk D., Barbour R., Dunn W. Immunization with amyloid-β attenuates Alzheimer-disease-like pathology in the PDAPP mouse.//Nature. 1999. V. 400(6740). pp 173-177]. Leading western companies developed several preparations [www.affi-ris.com/press_releases/press_release_mimoVAX_dec_|  |_06.pdf;  www.clini-cal-tri-als.gov/ct2/show/NCT0041 1580], however, none of them successfully passed clinical studies. The studies were suspended because 6% of patients receiving amyloid-β injections developed aseptic meningoencephalitis [Shenk D. Amyloid-β immunotherapy for Alzheimer's disease: the end of the beginning.//Nat. Rev. Neurosci. 2002. V. 3 (10). pp 824-828; Senior K. Dosing in Phasell trial of Alzheimer's vaccine suspended. Lancet. Neurol. 2002. V. 1 (1). pp 3]. These results call into question the safety of βA-based drugs as immunotherapeutic agents.

Moreover, the structural and histopathological changes observed in the brain of AD patients were determined to be neurofibrillary tangles and amyloid deposits. Binding the receptors of the finished products with the amyloid is thought to promote the penetration of the latter through the blood-brain barrier of the central nervous system and its accumulation as amyloid plaques, the main reason for Alzheimer's disease [Leclerc E., Sturchler E., Vetter S. The S 100B/RAGE Axis in Alzheimer's Disease. Cardiovasc. Psychiatry Neurol. 2010. V. 2010. pp 1-11]. The major component of the most prevalent neuritic amyloid plaques is the peptide comprising 40-42 amino acids called "Aβ4 amyloid peptide" (Price, D. L. andall, Drug Development Research (1985) 5:59-68).

Aβ4 amyloid peptide is a peptide formed in the proteolysis of membrane glycoproteins denoted with protein-precursors of Aβ4 amyloid peptide (βAPP). Said protein-precursors of the amyloid peptide consist of 695 to 770 amino acids, all of them encoded with the same gene.

Two major variants of Aβ4 amyloid peptides have been identified: Aβ40 and Aβ42; they have characteristically different tissue distribution both under physiological and pathological conditions. The variant with 42 amino acids is the dominant form in amyloid plaques located in the brain of AD patients. WO9927944 application discloses AD treatment with Aβ42 peptide injection, however, clinical studies of 360 patients with moderate to severe AD to whom Aβ42 peptide was administered as an antigen were suspended after some patients were diagnosed with encephalitis [Scrip Daily Online, 25 Feb. 2002, S007455320, The Scientist 16[7]: 22, Apr. 1, 2002].

Among other peptides proposed for the treatment of AD are the peptides developed in the IBCh of the RAS consisting of the amino acid sequences identified in: RU2372355, 2009, and RU2558242, 2015.

The latter can be considered the closest analog to the claimed agent. This drug affected behavior of experimental animals; however, its impact was insufficiently effective

SUMMARY OF THE INVENTION

The claimed invention achieves the objective of expanding the range of preparations with a therapeutic effect on Alzheimer's disease.

The claimed objective is achieved by preparing and using a peptide of the general formula acetyl-X-ARG-ARG-amide, where X—a sequence of D- and L-amino acid residues, such as ARG, MET, and LYS.

Hereinafter, when tetrapeptides are characterized, the D-L group of (X) amino acids will be given in parenthesis.

The conducted experiments demonstrated (Example 1, Table 3) that all aforementioned peptides exhibited a normalizing effect on the AD rat models, which was caused by their unique primary and spatial structure due to the amino acid residue being present in various stereo configurations. The best results were achieved when using tetrapeptide based on D- and L-amino acid residues of lysine (LYS).

The tetrapeptides were prepared according to the standard procedure for solid-phase peptide synthesis [J. M. Steward and, J. D. Young, "Solid Phase Peptide Synthesis", W.H. Freeman Co., San Francisco, 1969] followed by the removal of protecting groups and purification of the final product.

Specifically, the tetrapeptide (LYS) synthesis was conducted as follows:

To synthesize the peptide, 0.2 g N-tert-butyloxycarbonyl-Nω-mesitylenesulfonyl-arginyl-methyl-benzhydryl amino polymer in 10 ml of dimethylformamide were added to a reaction vessel. The peptide was then extended from the C-terminus according to the procedure shown in Table 1

TABLE 1

Procedure for adding one amino acid residue

| No | Procedure | Reagents | Number of repetitions | Time, min | Reagent volume, ml |
|---|---|---|---|---|---|
| 1 | Washing | Methylene chloride | 1 | 2 | 10 |
| 2 | Deprotection | 50% trifluoroacetic acid | 1 | 2 | 5 |
| 3 | Deprotection | 50% trifluoroacetic acid | 1 | 30 | 5 |
| 4 | Washing | Dimethylformamide | 3 | 1 | 10 |
| 5 | Neutralization | Diisopropylethylamine (5 mmol in dimethylformamide) | 1 | 1 | 5 |
| 6 | Condensation | 1.0 mmol oxybenzotrisol ester of the corresponding amino acid derivative | 1 | 30 | 5 |
| 7 | Washing | Dimethylformamide | 3 | 1 | 10 |
| 8 | Ninhydrin test/bromophenol blue -Pro/ | | | | |

When the ninhydrin test was positive, the condensation was repeated starting with #3. The prepared peptidyl-polymer was treated with anhydrous hydrogen fluoride and a crude product was isolated in accordance with the procedure outlined in Table 2.

TABLE 2

Peptidyl-polymer deprotection procedure and removal of the peptide from the polymer matrix

| No | Procedure | Reagents | Number of repetitions | Time min. | Temperature ° C. | Reagent volume ml |
|---|---|---|---|---|---|---|
| 1. | Full deprotection and peptide removal from polymer matrix | Anhydrous hydrogen fluoride/m-cresol (10:1 by volume) | 1 | 60 | 0 | 5 |
| 2. | Evaporation | | | | | |
| 3. | Washing, filtration | Absolute ether | 3 | 5 | | 25 |
| 4. | Washing from filter | Trifluoroacetic acid | 3 | — | — | 1 |
| 5. | Precipitation | Diethyl ether | | | | 100 |
| 6. | Filtration, washing | Diethyl ether | 3 | | | 10 |

The obtained crude products were purified by reverse phase high pressure chromatography on a C18 Nova Pack column, 19×300 mm, 300 Å, 2-50% gradient of acetonitrile in 0.1% trifluoroacetic acid. According to the optical density data, the peptide content was 99.5%. The amino acid content of the peptide and its molecular weight corresponded to the theoretical.

Other peptides were prepared in a similar manner with the corresponding adjustment of the initial component composition. The structure and homogeneity of the prepared peptides were confirmed by reverse phase high pressure chromatography data and amino acid and mass-spectra analyses.

BRIEF DESCRIPTION OF DRAWINGS

The properties of the tetrapeptides are illustrated with the following drawings.

INDUSTRIAL APPLICABILITY

Industrial applicability is illustrated with the following examples:

Example 1. Scopolamine-Induced Alzheimer's Disease Model

White random-bred adult male rats weighing 200-240 g were used. Groups of 7 animals per group were formed. 1st group—control, 2nd—pathology, 3rd—comparator drug, 4th-6th—neuropeptides.

Scopolamine was administered i.p. to the animals in all groups except for the control at a 1 mg/kg dose daily, once a day for 27 days. From the 28th day on, the animals in groups 2 and 3 were administered the comparator drug and the claimed preparation respectively over the course of 10 days. The drugs were administered daily, once a day.

An AchE inhibitor donepezil, which was entered into the AD treatment protocols in Russia, USA, and EU counties, was used at a 1 mg/kg dose as the comparator drug. The tetrapeptides were administered i.n at a 0.1 mg/kg dose. The animals in the pathology group received 0.9% sodium chloride solution i.n. and i.p. as a placebo.

After a course of treatment with the preparations, the CNS function of the animals was evaluated according to the open field (OF), extrapolation escape (EE), and conditioning passive avoidance reflex (CPAR) tests [Guidelines for conducting nonclinical studies of pharmaceuticals/edited by A. N. Mironov, MD, PhD, Part 1, M.: Grief and K, 2012-944 p.; Methods of behavior analysis in neuroscience—London, New York, Washington: CRCPress, 2001.-329 p.], and also The Porsolt swim test (PST) [Methods of behavior analysis in neuroscience—London, New York, Washington: CRCPress, 2001.-329 p; Porsolt R. D. Depression: A new animal model sensitive to antidepressant treatments/R. D. Porsolt, M. LePichon, M. Oalfre//Nature.—1977.—Vol. 266.—P. 730-732.].

The OF and EE tests were conducted on the 1st day, PST—on the 2nd day, CPAR—on the 1st and 10th day post treatment with the preparations. The CPAR proficiency criterium—remaining in the light area of the CPAR device during at least 180 sec. The antiamnesic action (AA) in the CPAR test was calculated using Butler's formula [K. S. Radionova. Original nootropic preparation Noopept ameliorates memory loss caused by the M- and N-choline receptor blockade in rats/K. S. Radionova, A. P. Bel'nik, R. U. Ostrovskaya//Bul experim. Biology and Medicine.—2008.—T.146, No 1.—pp 65-68]. After that, the animals were removed from the experiment by administering a narcotic, followed by decapitation. The brain was extracted and weighed, and the brain weight coefficient (BWC) was calculated. Immediately after extraction, the brain was frozen in liquid nitrogen and used in subsequent biochemical and histochemical studies. Glucose levels in whole arterial (common carotid artery) and venous (venous cerebral sinus) blood were determined by the glucose oxidase test, the difference in the arterial-venous glucose content was calculated (glucose consumption marker). The levels of average weight molecules—the toxic products of cell biodegradation damaged during the disease (nucleoside derivatives, peptoids, glucuronic acid salts, etc.) in the blood serum (AWM) were calculated [A. N. Kovalevsky. Notes on the screening method of determination average weight molecules/A. N. Kovalevsky, O. Ye. Nifantiev//Lab. Science. 1989 No 5, p. p. 35-39].

Standard biochemical methods were used to determine the content and activity of antioxidant defense enzymes and products of lipid peroxidation: malonic dialdehyde (MDA) [Modern Biochemistry Methods/[edited by V. N. Orekhovich]; M. Medicine, 1977, 392 pp]; superoxide dismutase (SOD) [O. P. Makarevich Activity of superoxide dismutase in blood in the acute period of various diseases/O. P. Makarevich, P. P. Golikov//Lab. Science, 1983, No 6, pp 24-27]; catalase [Methods for the Determination of Catalase Activity/M. A. Korolyuk, L. I. Ivanova, I. G. Mayorova, et al//Lab. Science, 1988, No 1, pp 16-19]; and reduced glutathione [T. A. Kochetov A Practical Guide to Enzymology. M. Nauka, 1980, 280 pp].

The content of acetylcholine in cerebral blood was determined by [Method for Determining Acetylcholine: RU2256920, 2005], cholinesterases (synaptic and total acetylcholinesterase, total butyrylcholinesterase) by methods [A. I. Panyukov On the Use of the Hestrin Method for Separate Measurement of Cholinesterase Activity/A. I. Panyukov//Issues of Med. Chemistry. 1966, t. 12, Edition 1, pp 88-95; Hajos E. An Improved Method for the Preparation of Synaptosomal ractions in high purity/E. Hajos//Brain Res.—1975.—Vol. 93.—No 3.—pp. 485-489.], serotonin by [Atack C. A procedure for the isolation of noradrenaline (together with adrenaline), dopamine, 5-hydroxy tryptamine and histamine from the same tissue sample using a single column of strongly acidic cation exchange resin 1C. Atack, T. Magnusson//ActaPharma-colToxicol (Copenh).—1978.—Vol. 42 (1).—pp 35-57], adenosine triphosphate acid (ATP)—[N. D. Yeschenko. Determination of ATP content in tissue//Methods for biochemical research/Edited by prof. M. I. Prokhorova, Leningrad, pub. House LSU, 1982.—pp. 256-258].

The quantitative data were statistically processed. The results are presented as the mean error and standard error of the mean (M±m). Student's t-test or Mann-Whitney test were used to evaluate the statistical significance of the between-group variances depending on the frequency distribution pattern. The difference in the results considered in an alternative form was evaluated by the Fisher transformation φ. Statistical significance of the intra-group variances was determined by using Wilcoxon paired t-test. The correlation analysis was conducted by calculating Spearman's rank correlation coefficient ρ.

The neuroprotective activity of the tetrapeptide was determined by integral estimation of functional, biochemical, and histological test results.

Results of the medication's effect on the mobility, orientation, exploratory activity, and emotional reaction of the rats and their vegetative reactions in the OF test are shown in Table 3.

The data in Table 3 demonstrate that the tested peptides restore the orientation and exploratory activity of rat models with AD. This is demonstrated by a statistically significant increase in the number of surveyed open areas in the OF test (up to 52%, p<0.05). The best results were obtained for tetrapeptide (LYS). The data demonstrate that the tetrapeptide can normalize behavioral reactions of animal models with AD. The tested pharmaceutical also normalizes emotional reactions of rats in the OF, reduces the number of grooming acts by 44.7% (p<0.05), which characterizes its activity as stress-protecting.

The EE test shows the ability of tetrapeptide (LYS) to improve the cognitive functions of rat models with AD (Table 4).

TABLE 4

Effect of tetrapeptide (LYS) and the comparator drug donepezil on cognitive functions of rat models with Alzheimer's disease in the exploratory escape test

| | | Scopolamine 1 mg/kg i.p., 27 days | | |
|---|---|---|---|---|
| Indicators (3 min) | Control (n = 6) | Pathology (n = 7) | Donepezil 1 mg/kg i.p. 10 days (n = 7) | Peptide (LYS) 0.1 mg/kg i.n. 10 days (n = 7) |
| Escape time, sec. | 37.17 ± 8.51 | 41.29 ± 13.12 | 18.86 ± 3.57 | 11.00 ± 3.07*^ |
| % of animals succeeded | 100% | 100% | 100% | 100% |

Note.
Statistically significant differences ($p < 0.05$):
*with control group,
^with pathology group.

Compared to the pathology group, tetrapeptide (LYS) statistically significantly reduces the time (3.8 times) the rats need to burrow under the cylinder edge (escape) in the EE test ($p<0.05$). This is 41.7% higher than the time for donepezil ($p<0.05$). There is no difference in the number of successful animals (burrowed) in each group. The tetrapeptide's (LYS) ability to stimulate the cognitive functions of animal models with a neurogenerative disease is one of the indicators of its nootropic activity.

Figure 1:
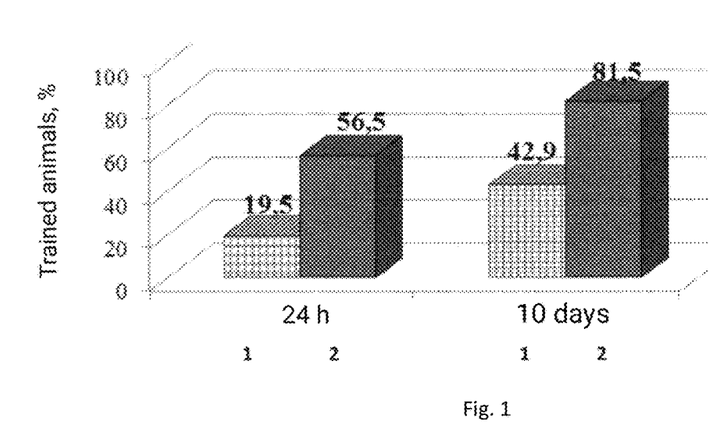
FIG. 1 shows the effect of tetrapeptide (LYS) and the comparator drug donepezil on the acetylcholinesterase activity in Alzheimer's disease rat model brain synaptosomes. The antiamnesic action of the tetrapeptide and donepezil presented on the first and tenth day after a treatment regimen of rat models with Alzheimer's disease I (conditioned passive avoidance reflex) is shown based on a percentage of total trained animals. 1.—donepezil at a 1 mg/kg dose; 2—tetrapeptide at a 0.1 mg/kg dose.

Another element of the nootropic activity of tetrapeptide (LYS) apparent in the animal models with AD is its antiamnestic activity. Results of the CPAR test are shown in Table 5 and in FIGS. 1 and 2.

TABLE 5

Latent period in rat models with Alzheimer's disease entering the dark area of the CPAR device

| | Latent period of entry into the dark area of the CPAR device, sec. | | |
|---|---|---|---|
| Group, n | Initial | In 24 hrs. | In 10 days |
| Control (n = 7) | 18.71 ± 3.52 | 167.86 ± 11.49 | 99.86 ± 17.06 |
| Pathology (scopolamine) (n = 7) | 20.29 ± 5.54 | 70.29 ± 16.44* | 38.86 ± 11.62* |
| Scopolamine + donepezil 1 mg/kg (n = 7) | 24.00 ± 6.23 | 93.29 ± 26.11* | 69.43 ± 11.10^ |
| Scopolamine + tetrapeptide (LYS) 0.1 mg/kg i.n. (n = 7) | 20.14 ± 3.73 | 126.14 ± 23.62 | 89.71 ± 19.09^ |

Note.
Statistically significant differences ($p < 0.05$):
*with control group,
^with pathology group.

The pathology group showed a reduced time of entry into the dark area of the device, which is typical for a cholinergic neurotransmission blockade, and which is indicative of the amnestic action.

Analysis of Table 5 data demonstrates that tetrapeptide (LYS) increases the latent period of rat models with AD entering the dark area of the CPAR device both 24 hrs. post its formation (by 79.5% compared to the pathology group) and post 10 days (by 130.9% compared to the pathology group, $p<0.05$). An increase in this result with the tetrapeptide (LYS) preparation attests to its positive effect on the formation of the conditioned retentive memory reflex in animals (positive nootropic effect). According to this indicator, the tested tetrapeptide (LYS) preparation surpasses donepezil. The AA of the tetrapeptide (LYS) peptide on the first day was 56.5% (FIG. 1), and on the 10th day, it increased to—81.5%. The same results for donepezil are less than those in the tetrapeptide (LYS) group in 2.9 and 1.9 times respectively.

Thus, the examined tetrapeptide (LYS) exhibited a significant choline-positive action in the cognitive disorder model resulting from reduced cholinergic transmission. The tetrapeptide's cytokine-mediated anti-inflammatory properties may result from the effect of the tetrapeptide on the central cholinergic neurons directly involved in the release of pro- and anti-inflammatory cytokines.

Figure 2:
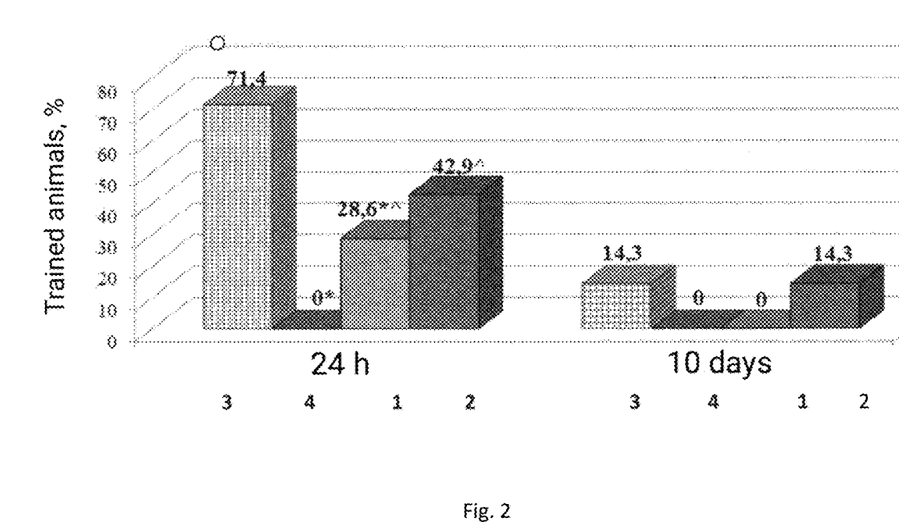
FIG. 2 shows the effect of tetrapeptide (LYS) and the comparator drug donepezil on the number of rat models with Alzheimer's disease who reached a proficiency criterium in the conditioned passive avoidance reflex on the 1st and 10th day post therapy, based on a percentage of total trained animals. (Statistically significant difference ($p>0.05$): *—control group, ^—pathology group.) 1—donepezil at a 1 mg/kg dose; 2 tetrapeptide at a 0.1 mg/kg dose, 3—control, 4—pathology.

On the first and tenth days post CPAR training, all the rats in the pathology group entered the dark area of the device in less than 3 min. (FIG. 2). This is indicative of hypomnesia resulted from the model pathology. On the first day, donepezil statistically significantly increases the number of animals who reached the CPAR learning criterium, up to 28.6% ($p<0.05$ with the pathology group). However, in ten days, its activity goes down to the level of the pathology group. Contrary to donepezil, tetrapeptide (LYS) increases said indicator both on the first and the tenth day to 42.9% ($p<0.05$ with the pathology group) and 14.3% respectively. This result is indicative of the positive effect of tetrapeptide (LYS) on the nootropic functions of rat models with AD.

Thus, the CPAR test demonstrated that oligopeptide neuroprotector tetrapeptide (LYS) exhibits positive nootropic properties, high antiamnestic activity, and increase number of animals in the groups reaching the conditioning reflex learning criterium in rat models with AD.

Tetrapeptide (LYS) shows a tendency to reduce the level of depressive symptomatology in rat models with AD (Table 6).

TABLE 6

Effect of tetrapeptide (LYS) and the comparator drug donepezil on
the performance of rat models with AD in the Porsolt swim test

| Group | Indicators | | |
|---|---|---|---|
| | Latent period of immobilization, sec | Number of immobilization acts | Total duration of immobilization, sec |
| Control (n=7) | 65.82 ± 3.14 | 8.26 ± 1.13 | 104.11 ± 9.15 |
| Pathology (n = 7) | 52.71 ± 8.25 | 7.71 ± 0.52 | 149.00 ± 27.75 |
| Donepezil 1 mg/kg, i.p. (n = 7) | 69.43 ± 12.64 | 9.29 ± 1.66 | 144.29 ± 21.59 |
| Tetrapeptide (LYS) 0.1 mg/kg i.n. (n = 7) | 68.12 ± 6.15 | 6.21 ± 0.82 | 111.06 ± 13.25 |

Analysis of Table 6 data demonstrates that the pathology group of rats tends to develop depressive symptomatology. It is expressed as a latent period of the first immobilization, an increased number and total duration of immobilization acts. Tetrapeptide (LYS) reduces the total duration and the number of motionless delays (immobilizations) of the rats and increases the latent period of the first immobilization as a trend, which characterizes its activity as anti-depressive.

Thus, a combination of functional CNS tests of rat models with AD showed a combined nootropic effect of tetrapeptide (LYS) expressed in the normalization of orientation and exploratory activity of the animals in the OF, stimulation of their cognitive functions, and positive nootropic effect. The nootropic activity shown on AD models is followed by its tendency to reduce the depressive symptomatology of the animals resulting from the model pathology.

Figure 3:
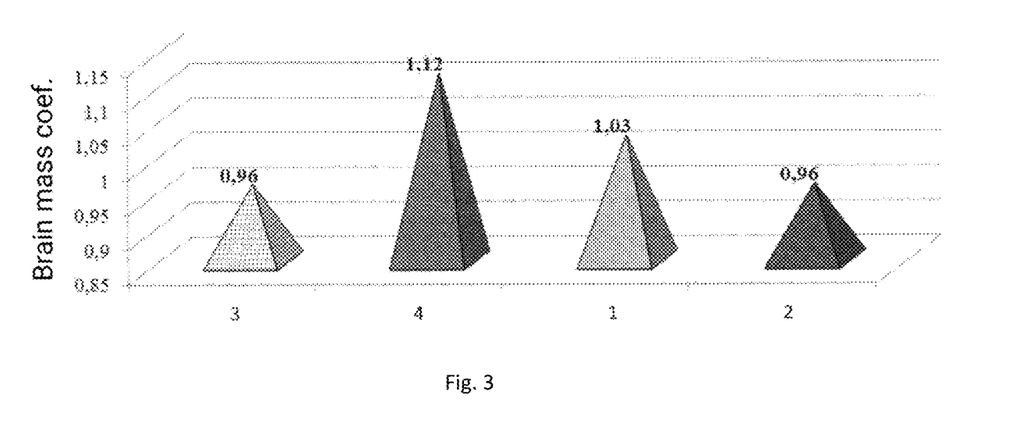
FIG. 3 shows the effect of tetrapeptide (LYS) and the comparator drug donepezil on the brain weight coefficient (i.e. brain mass coef.) in rat models with Alzheimer's disease. 1—donepezil at a 1 mg/kg dose; 2 tetrapeptide at a 0.1 mg/kg dose, 3—control, 4—pathology.
Figure 4:
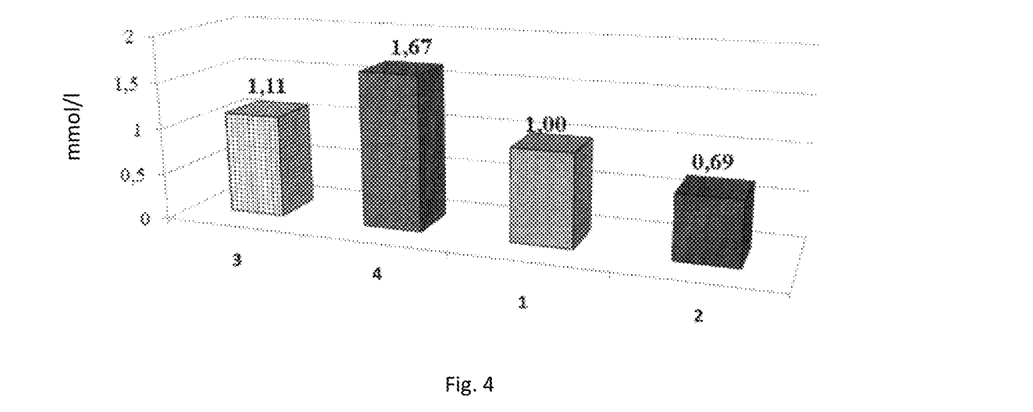
FIG. 4 shows the effect of tetrapeptide (LYS) and the comparator drug donepezil on the arteriovenous difference in rat models with Alzheimer's disease. 1—donepezil at a 1 mg/kg dose; 2—tetrapeptide at a 0.1 mg/kg dose, 3—control, 4—pathology.
Figure 5:
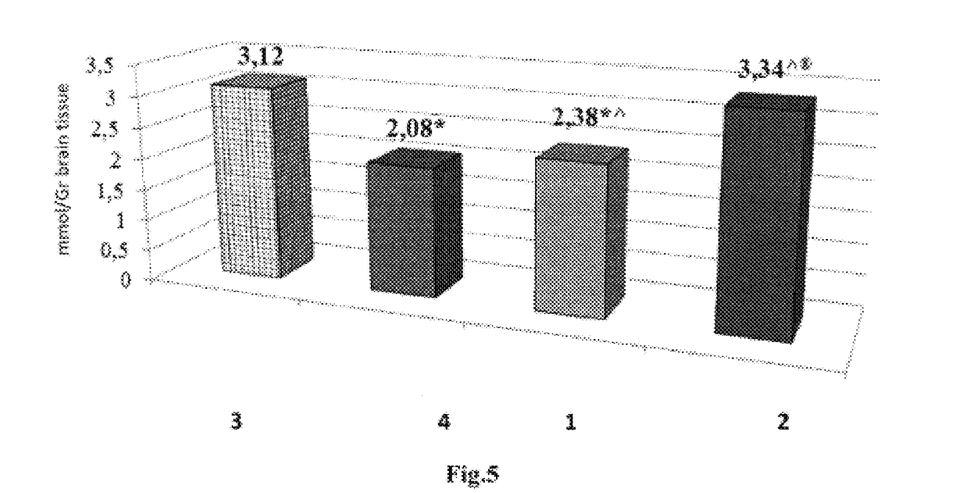
FIG. 5 shows the effect of tetrapeptide (LYS) and the comparator drug donepezil on the brain ATP level in rat models with Alzheimer's disease 1 donepezil at a 1 mg/kg dose; 2—tetrapeptide at a 0.1 mg/kg dose, 3—control, 4—pathology. Statistically significant difference ($p>0.05$): *—with control group, ^—with pathology group, ®—with donepezil group.

Tetrapeptide (LYS) was found to have a tendency to normalize the BWC (FIG. 3). In the pathology group, this factor increased by 16.7%, which is statistically insignificant compared to the control. Both donepezil and (LYS) also statistically insignificantly reduce the BWC by 8.0% and 14.3% respectively (tetrapeptide (LYS) completely normalizes this function). The BWC normalization may also occur due to the membrane-stabilizing effect of tetrapeptide (LYS) [R. D. Deyko The effect of the potential neuroprotector acetyl-D-Lys-Lys-Arg-Arg-amide on neurodestruction and neuroapoptosis in rats during a cerebrovascular accident/R. D. Deyko, S. Yu. Shtrygol, et al.//Pharmaceutical Herald.—2016.—No 1(71).—pp 96-102], which occurs in model AD, by reducing the cholinergic neuron alteration.

Figure 6:
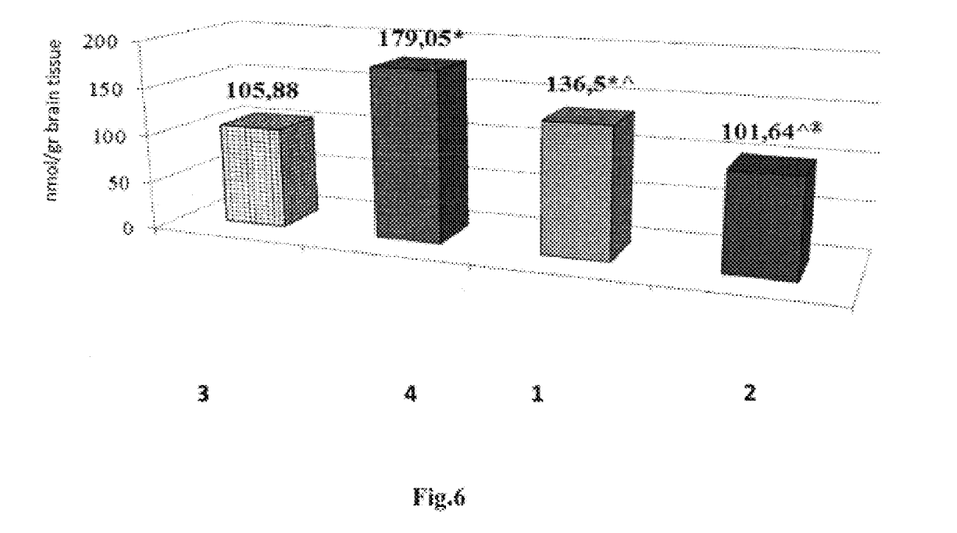
FIG. 6 shows the effect of tetrapeptide (LYS) and the comparator drug donepezil on the serotonin level in the brain of rat models with Alzheimer's disease 1—donepezil at a 1 mg/kg dose; 2—tetrapeptide at a 0.1 mg/kg dose, 3—control, 4—pathology. Statistically significant difference ($p>0.05$): *—with control group, ^—with pathology group, ®—with donepezil group.

The effect of tetrapeptide (LYS) and donepezil on the reactively produced overexpression of serotonin is also positive (FIG. 6). They reduce the level of this neurotransmitter by 23.8% and 43.2%, respectively. Tetrapeptide (LYS) reduces this factor, resulting in its normalization, which is confirmed by the absence of statistically significant differences from the control group.

Figure 7:
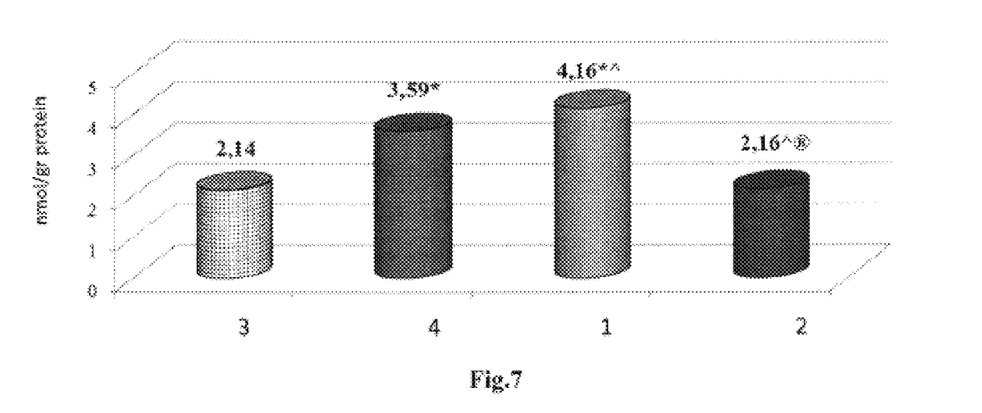
FIG. 7 shows the effect of tetrapeptide (LYS) and the comparator drug donepezil on the malonic aldehyde content in the brain of rat models with Alzheimer's disease 1—donepezil at a 1 mg/kg dose; 2—tetrapeptide at a 0.1 mg/kg dose, 3—control, 4—pathology. Statistically significant difference ($p>0.05$): *—with control group, ^—with pathology group, ®—with donepezil group.

The tetrapeptides were found to have a positive effect on the antioxidant protection system in the brains of rat models with Alzheimer's disease. The tetrapeptide reduces the content of the secondary product of peroxide oxidation, malonic aldehyde (MAD,) in the brain (FIG. 7). The comparator drug donepezil, on the other hand, increases its content by 15.9% as compared to the pathology group. This reduction caused by the tetrapeptide is 39.8% relative to the pathology group.

Figure 8:
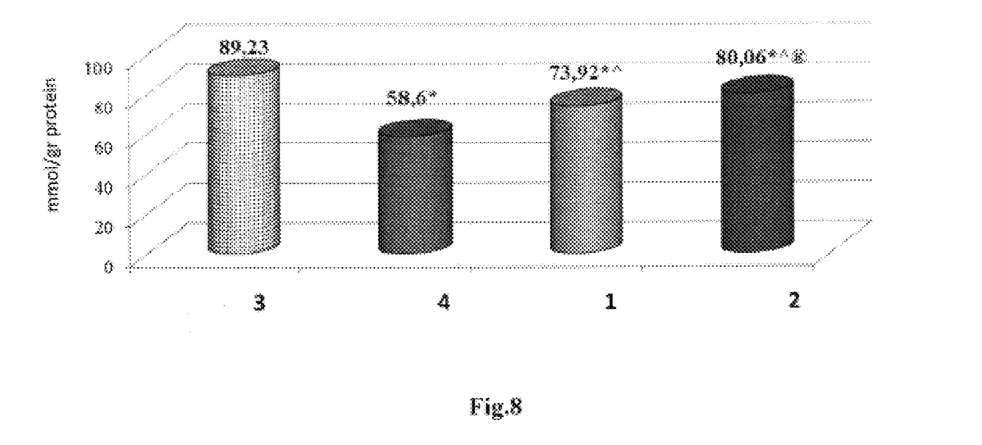
FIG. 8 shows the effect of tetrapeptide (LYS) and the comparator drug donepezil on the reduced glutathione level in the brain of rat models with Alzheimer's disease 1—donepezil at a 1 mg/kg dose; 2—tetrapeptide at a 0.1 mg/kg dose, 3—control, 4—pathology. Statistically significant difference ($p>0.05$): *—with control group, ^—with pathology group, ®—with donepezil group.

Tetrapeptide (LYS) significantly increases the level of the reduced glutathione, which is statistically significantly reduced by 34.3% (p<0.05 to the control group) in the Alzheimer's disease model (FIG. 8). This increase caused by the tetrapeptide is 36.6%.

Figure 9:
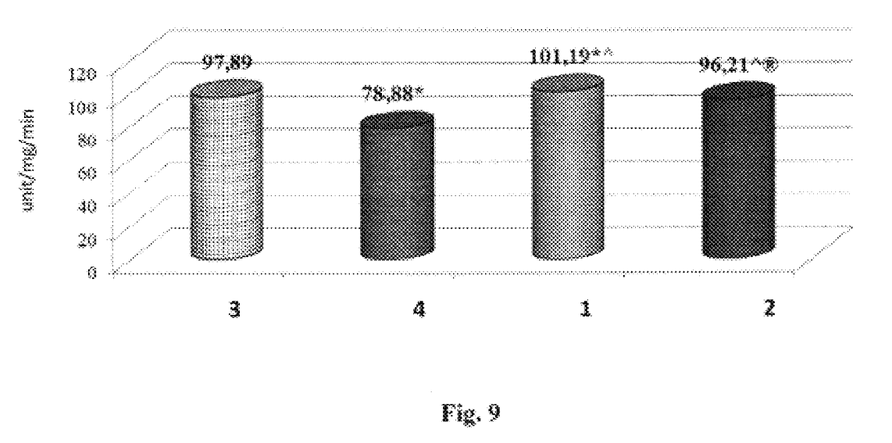
FIG. 9 shows the effect of tetrapeptide (LYS) and the comparator drug donepezil on the superoxide dismutase activity in the brain of rat models with Alzheimer's disease 1—donepezil at a 1 mg/kg dose; 2—tetrapeptide at a 0.1 mg/kg dose, 3—control, 4—pathology. Statistically significant difference ($p>0.05$): *—with control group, ^—with pathology group, ®—with donepezil group.

The tetrapeptide has a profound effect on SOD in the brain of rat models with AD (FIG. 9). It increases the SOD activity by 22% as compared to that of the pathology group, which in turn, increases the antioxidant protection of the brain in the AD models.

Figure 10:
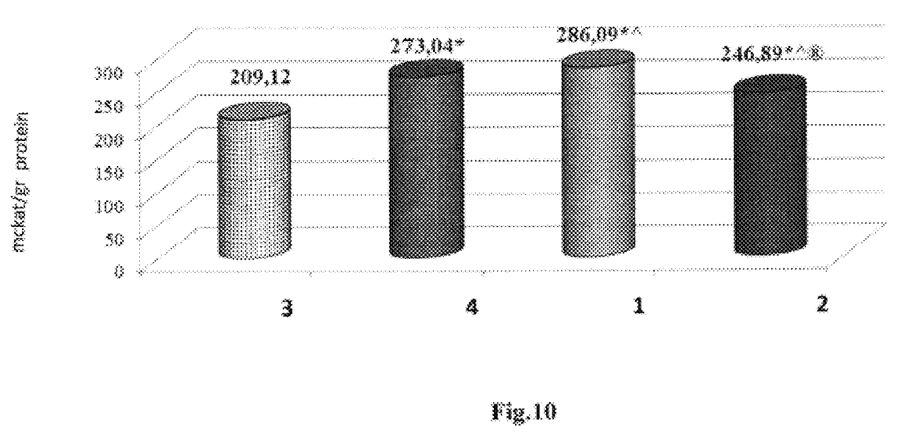
FIG. 10 shows the effect of tetrapeptide (LYS) and the comparator drug donepezil on the catalase activity in the brain of rat models with Alzheimer's disease 1—donepezil at a 1 mg/kg dose; 2—tetrapeptide at a 0.1 mg/kg dose, 3—control, 4—pathology. Statistically significant difference ($p>0.05$): *—with control group, ^—with pathology group, ®—with donepezil group.

FIG. 10 shows that tetrapeptide (LYS) reduces the elevated activity of catalase, compensatory-occurring in AD models, in 1.1 times, which is statistically significant.

Thus, tetrapeptide (LYS) makes an effective impact on the antioxidant protection system of the brain in rat models with AD. It increases the level of reduced glutathione and SOD activity in pathologies and decreases the brain's need for overexpression of catalase, the enzyme responsible for decomposing peroxides, the final products of peroxide modification of protein and lipid substrates. This activity results in a significant reduction of the level of MDA, an intermediate product of peroxide modification of lipids constituting a large part of biomembrane neurons. This indirectly confirms the tetrapeptide's membrane-stabilizing properties taking place both during cerebrovascular and neurodegenerative diseases.

Figure 11:
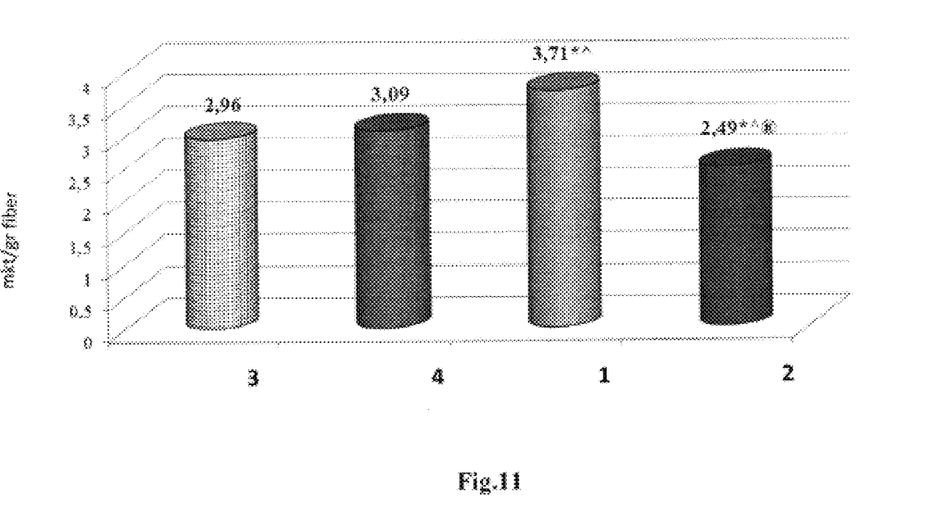
FIG. 11 shows the effect of tetrapeptide (LYS) and the comparator drug donepezil on the acetylcholine content in the brain homogenate of rat models with Alzheimer's disease 1—donepezil at a 1 mg/kg dose; 2—tetrapeptide at a 0.1 mg/kg dose, 3—control, 4—pathology. Statistically significant difference ($p>0.05$): *—with control group, ^—with pathology group, ®—with donepezil group.

As becomes evident from analyzing FIG. 11 data, tetrapeptide (LYS) statistically significantly reduces the content of acetylcholinesterase in the brain of rat models with AD compared to the control, pathology, and donepezil groups (p<0.05).

Figure 12:
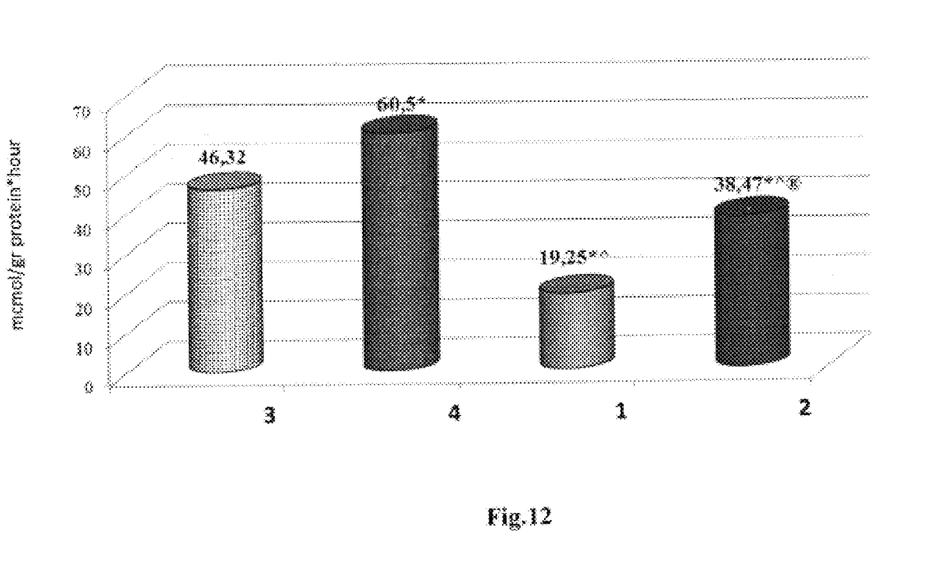
FIG. 12 shows the effect of tetrapeptide (LYS) and the comparator drug donepezil on the acetylcholinesterase activity in brain synaptosomes of rat models with Alzheimer's disease 1—donepezil at a 1 mg/kg dose; 2—tetrapeptide at a 0.1 mg/kg dose, 3—control, 4—pathology. Statistically significant difference ($p>0.05$): *—with control group, ^—with pathology group, ®—with donepezil group.
Figure 13:
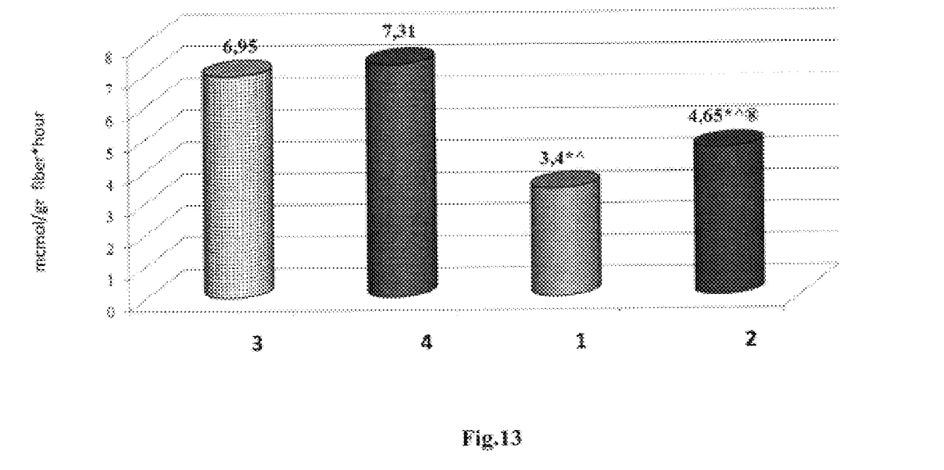
FIG. 13 shows the effect of tetrapeptide (LYS) and the comparator drug donepezil on the acetylcholinesterase activity in whole brain homogenates of rat models with Alzheimer's disease 1—donepezil at a 1 mg/kg dose; 2—tetrapeptide at a 0.1 mg/kg dose, 3—control, 4—pathology. Statistically significant difference ($p>0.05$): *—with control group, ^—with pathology group, ®—with donepezil group.
Figure 14:
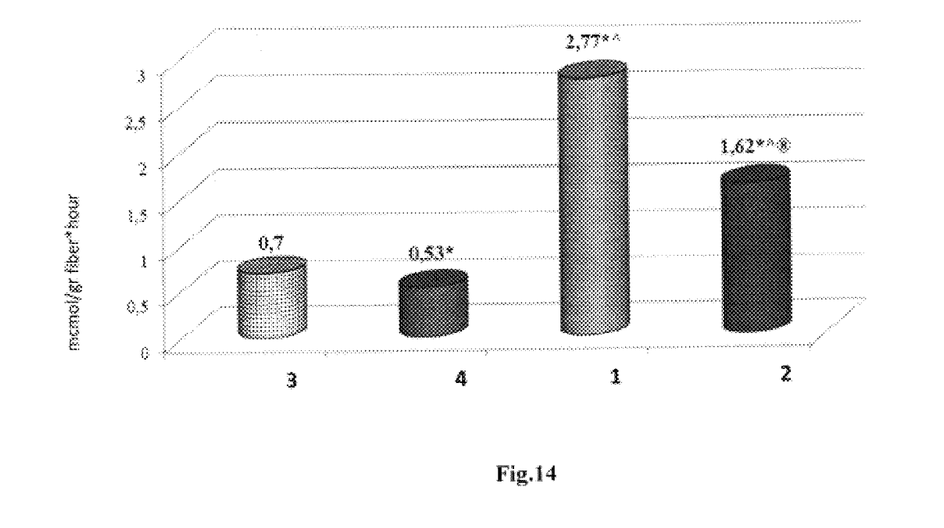
FIG. 14 shows the effect of tetrapeptide (LYS) and the comparator drug donepezil on the butyrylcholinesterase activity in whole brain homogenates of rat models with Alzheimer's disease 1—donepezil at a 1 mg/kg dose; 2 tetrapeptide at a 0.1 mg/kg dose, 3—control, 4—pathology. Statistically significant difference ($p>0.05$): *—with control group, ^—with pathology group, ®—with donepezil group.

Similar to donepezil, tetrapeptide (LYS) reduces the AChE activity (FIGS. 12 and 13) both in synapsosomes and in the whole brain homogenate, which results in the formation of an average negative bond between the activity of this enzyme and the acetylcholinesterase content in the brain tissue. Moreover, the tetrapeptide significantly increases the butyrylcholinesterase activity, which is reduced in the brain of animal models with AD, although, it doesn't take part in the inactivation of acetylcholine (FIG. 14)

The effect of the tested peptide on the acetylcholinesterase activity and acetylcholine content in the brain was thereby established. It reduces both the Ach amount and the activity of acetylcholinesterase that inactivates acetylcholine. This results in improved cognitive and nootropic functions of rat models with AD.

Example 2. Study of Antidepressant Properties of (LYS) on Reserpine-Induced Depression Models The experiment was conducted on 16 white random-bred adult male rats weighing:

180-220 g. The antidepressant activity of tetrapeptide (LYS), a neuroprotector, at a 0.02 mg/kg dose intranasally (i.n.) was evaluated. Imipramine, a classic tricyclic antidepressant, was used as the comparator drug at a 15 mg/kg dose (melipramin, EGIS, Hungary) intraperitoneally (i.p.). The experiment was conducted in two stages. At the first stage, the intact animals were divided into two groups; 1—control group (n=5), 2—"imipramine" group (15 mg/kg i.p., n=6), 3—"tetrapeptide (LYS)" group (0.02 mg/kg i.n., n=5). 25-30 min. prior to the start of the experiment, the animals were administered their respective drugs. The animals in the control group were administered 0.9% NaCl solution i.p. and i.n. in the volume equal to the volume of the medications. After that, the animals of all groups were placed in the open field (OF) for 3 min., and their locomotor (number of crossed squares), orientation, and exploratory (number of upright positions and explored openings) activity as well as their emotional reactions (fecal boluses, urination, grooming) were evaluated. The indicators of depression in the animals (latent immobilization period, the number of such instances, and their total duration) were evaluated in the Popsolt swim test (PST) over 6 min. In the next 2 days, all the medications were administered at the same dose once a day; the last administration—30 min before the depressogenic sympatholytics of reserpine. Reserpine was administered on the 3rd day (2nd stage of the experiment) at a 4 mg/kg dose i.p. (as a suspension stabilized with Tween-80). Animals in all 3 groups were evaluated 6-7 hr. later in the OF and PST.

Test results were statistically processed. When the data distribution was normal, the parametric Student's t-distribution test was applied, when it was absent, the non-parametric MannWhitney U-test was used. When processing the results in an alternative form (presence/absence of the indicator), Fisher's angular transformation φ was applied. Wilcoxon paired t-criterium test was used for the intra-group statistical evaluation of the changed in the animal test results prior and post simulated depression. The results were considered to be statistically significant when p<0.05. The OF test results are shown in Table 7.

TABLE 7

Effect of tetrapeptide (LYS) and the comparator drug imipramine on test results of intact animals and animals with reserpine-induced depression in the Open Field Test, M ± m

| Test result | Experimental condition | Group, n | | |
|---|---|---|---|---|
| | | Control n = 5 | Imipramine n = 6 | Tetrapeptide (LYS) n = 5 |
| Locomotor activity (number of squares) | I | 18.4 ± 4.79 | 9.6 ± 1.53 | 4.0 ± 1.34*^ |
| | R | 4.4 ± 0.87 (−70.0%)® | 2.0 ± 0.55* (−79.17%)® | 3.4 ± 2.4 (−15.0%) |
| Orientation and exploratory activity (number of explored openings and upright positions) | I | 13.2 ± 3.64 | 6.8 ± 0.77 | 5.8 ± 0.77* |
| | R | 2.6 ± 1.63 (−93.18%)® | 1.6 ± 0.4* (−76.47%)® | 4.6 ± 2.4 (−20.69%) |
| Emotional reactions and concomitant vegetative state (total number of grooming acts, fecal boluses, and urinations) | I | 1.6 ± 0.58 | 4.6 ± 0.58* | 1.8 ± 0.77^ |
| | R | 3.0 ± 0.55 (+87.5%) | 2.8 ± 1.39 (−39.12%) | 0.2 ± 0.2* (−88.9%)® |
| Sum of all results | I | 33.2 ± 8.43 | 20.8 ± 2.68 | 11.6 ± 2.49*^ |
| | R | 10.0 ± 1.30 (−97.0%)® | 6.4 ± 1.6® (−69.23%)® | 8.2 ± 4.98 (−29.3%) |

Note.
I - intact animals;
R - reserpine-induced depression;
p ≤ 0.05:
*control group,
^imipramine group,
®between test results prior and post simulated depression;
in parentheses - % change in test results for animals with reserpine-induced depression vs. corresponding results for intact animals.

Table 7 demonstrates that tetrapeptide (LYS) suppresses all types of activities and emotional reactions in the OF in the intact animals. Imipramine also tends to suppress the locomotor, orientation, and exploratory activity of the intact animals, on the contrary, it increases the number of emotional reactions 2.9 times, p<0.05, as compared to the control). Thus, in the OF test, tetrapeptide (LYS) exhibits a more pronounced sedative effect than the comparator drug imipramine in the animals with no depression.

Reserpine causes severe model depression (Table 7) marked by reduced motor (by 70% p<0.05 compared to that of the intact animals), orientation and exploratory activity (by 93.2%, p<0.05 compared to that of the intact animals), as well as a tendency to the increased level of emotional reactions (1.9 times). The sum of all these types of activities is decreased by 97% (p<0.05). Imipramine reduces the degree of these disorders only insignificantly. The locomotor activity is reduced by 79.2% (p<0.05 compared to those of the intact animals), and the orientation and exploratory activity—by 76.5% (p<0.05 compared to those of the intact animals). The emotional reaction level is decreased insignificantly, 1.6 times (p>0.05 compared to that of the intact animals), but the sum of all types of activities is reduced significantly (by 69.2%, p<0.05), although not as pronounced as in the control. The reduction of the locomotor, orientation, and exploratory activities in the animals with reserpine-induced depression who were treated with tetrapeptide (LYS) was the least pronounced. It decreased the number of crossed squares only as a trend, 15%, while the orientation and exploratory activity—by 20.7% (p>0.05 compared to that of the intact animals). The sum of all types of activities for the animals treated with tetrapeptide (LYS) was reduced statistically insignificantly, by 29.3% (p>0.05 compared to that of the intact animals). The least pronounced reduction in all types of activities as compared to the control group and the imipramine group confirms the antagonistic action of tetrapeptide (LYS) against the depressive effect of reserpine. Only the sum of the emotional reaction and the concomitant vegetative reaction indicators is statistically significantly reduced, 9 times (p<0.05 compared to that of the intact animals), while on the other hand, it increased in the untreated animals.

Table 8 demonstrates that according to the PST results, tetrapeptide (LYS) exhibits an antidepressant effect both on the intact animals and on the animals with reserpine-induced depression. The antidepressant effect of tetrapeptide (LYS) on the intact animals is expressed in its ability to statistically significantly increase the latent immobilization period (3.5 times compared to the control, p<0.05) and reduce the number of immobilization periods and their total duration (11.5 and 16.1 times respectively, p<0.05 with the control).

duration 3.6 times (p<0.05 compared to the control. According to these results, the oligopeptide's activity exceeds that of imipramine.

Tetrapeptide (LYS), therefore, was found to exhibit a pronounced antidepressant effect in both intact animals and the animals with reserpine-induced depression. This suggests that it can beneficially modulate the monoaminergic transmission in the brain both in the normal state and model pathology induced by reserpine.

Analysis of the obtained results demonstrated that tetrapeptide (LYS), administered intranasally at a 0.1 mg/kg dose over 10 days once a day exhibited a long-lasting nootropic effect on the scopolamine-induced Alzheimer's disease model. The latter is expressed in the high antiamnesic activity of tetrapeptide (LYS) in the conditioned passive avoidance reflex test, lasting at least 10 days; its ability to stimulate cognitive functions of animals in the extrapolation escape test; normalize behavior in the open field test (improve orientation and exploratory activity and reduce the animals' reaction to stress). Additionally, there was a trend noticed towards reduced depressive symptomatology of rats treated with tetrapeptide (LYS).

The neuroprotective properties in rat models with AD are demonstrated as a trend to reduce the brain weight coefficient, increase the amount of cerebral serotonin, and optimize the carbohydrate metabolism in the brain (improved

TABLE 8

Effect of tetrapeptide (LYS) on intact rats and animals with reserpine-induced depression in the Popsolt swim test, M ± m

| Test result | Experimental condition | Group, n | | |
|---|---|---|---|---|
| | | Control n = 5 | Imipramine n = 6 | Tetrapeptide (LYS) n = 5 |
| Latent immobilization period, sec. | I | 61.8±18.5 | 106.8 ± 25.0 | 214.6 ± 66.7* |
| | R | 38.2 ± 17.2 (−39.2%) | 128.8 ± 44.5 (+20.6) | 170.8 ± 34.1* (−20.4) |
| Number of immobilization episodes | I | 13.8 ± 3.08 | 5.8 ± 1.6* | 1.2 ± 0.6* |
| | R | 7.8 ± 0.96 (−43.5%) | 5.2 ± 1.13 (−10.3%) | 3.0 ± 0.38* (+150.0%) |
| Total duration of immobilization, sec | I | 64.4 ± 32.5 | 18.0 ± 6.9 | 4.0 ± 2.7* |
| | R | 28.2 ± 8.81 (−56.2%) | 17.7 ± 5.8 (−1.7%) | 7.8 ± 2.3* (+95.0%) |

Note.
I- intact animals;
R- reserpine-induced depression;
*statistically significant differences with control group (p ≤ 0.05);
in parentheses - % change in test results for animals with reserpine-induced depression vs. corresponding results for intact animals.

The only statistically significant reduction in the animals treated with imipramine was observed in the number of immobilization episodes (p<0.05 compared to the control), while only a trend was observed towards the change in its latent period and total duration. This corresponds to the well-known fact of a gradual development of the specific effect of classic antidepressants, including tricyclic antidepressants, such as imipramine. Thus, the antidepressant effect of the tested peptide is not only decidedly powerful but also fast-acting.

Tetrapeptide (LYS) also exhibits a statistically significant antidepressant effect compared to that of the control against reserpine-induced depression. As is in the case with the intact animals, tetrapeptide (LYSO increases the latent immobilization period 4.5 times (p<0.05 compared to the control), reduces the number of immobilization episodes 2.6 times (p<0.05 compared to the control) and their total glucose utilization and increased ATP level). Also demonstrated were a pronounced antioxidant effect of tetrapeptide (LYS) exhibited in the reduced number of lipid peroxidation products in the brain, increase activity of antioxidant defense enzymes (superoxide dismutase) or reduced compensatory hyperactivity thereof (catalase).

The pronounced antidepressant effect of tetrapeptide (LYS) was observed in both intact animals and in the animals with reserpine-induced depression. The latter was expressed as statistically significant reduction in depressive symptomatology (immobilization).

Based on the combination of the determined pharmacological properties, tetrapeptide (LYS) has a potential for future clinical applications as a nootropic agent, a neuroprotector, and an antidepressant.

What is claimed is:

1. A peptide comprised of a general formula: acetyl-X-ARG-ARG-amide, wherein X=-(D-ARG)-ARG- or -(D-MET)-MET-, said peptide exhibiting an antidepressant activity and/or a therapeutic effect against Alzheimer's disease.

* * * * *

SEQUENCE LISTING

```
<160> NUMBER OF SEQ ID NOS: 1

<210> SEQ ID NO 1
<211> LENGTH: 3
<212> TYPE: PRT
<213> ORGANISM: Artificial Sequence
<220> FEATURE:
<221> NAME/KEY: Variant
<222> LOCATION: (1)-(2)
<223> OTHER INFORMATION: The peptide sequence, where X- DArg-Arg,
      DLys-Lys, and DMet-Met

<400> SEQUENCE: 1

Xaa Arg Arg
1
```